United States Patent [19]
Gaffar

[11] Patent Number: 5,753,633
[45] Date of Patent: May 19, 1998

[54] METHOD OF INHIBITING BONE RESORPTION

[75] Inventor: Abdul Gaffar, Princeton, N.J.

[73] Assignee: Colgate-Palmolive Company, New York, N.Y.

[21] Appl. No.: 843,042

[22] Filed: Apr. 11, 1997

[51] Int. Cl.$^6$ .................................................. A61K 31/675
[52] U.S. Cl. ............................ 514/79; 514/89; 514/91
[58] Field of Search ............................... 514/79, 89, 91

[56] References Cited

U.S. PATENT DOCUMENTS

| | | | |
|---|---|---|---|
| 3,941,772 | 3/1976 | Ploger et al. | 514/79 |
| 3,988,443 | 10/1976 | Ploger et al. | 514/79 |

OTHER PUBLICATIONS

Journal of Bone and Mineral Research; vol. 6, No. 10, 1991, pp. 1037–1942; "Effects of Potassium Peroxydiphosphate on Bone Resorption".

Bone 8, Supp. 1, S23–S28 (1987); "Bisphosphonates—History and Experimental Basis", H. Fleisch.

"Effect of Phosphate, Calcium and Magnesium on Bone Resorption and Hormonal Responses in Tissue Culture", Raisz and Niemann, Departments of Pharmacology and Medicine, University of Rochester School of Medicine and Dentistry, Rochester, NY, Sep. 1969 pp. 446–452.

*Primary Examiner*—Jerome D. Goldberg
*Attorney, Agent, or Firm*—Henry S. Goldfine

[57] ABSTRACT

A method is disclosed for inhibiting bone resorption, concomitant with the overproduction of PTH associated with hyperparathyroidism or secondary hyperparathyroidism, by providing a azacycloalkane-2,2-diphosphonic compound.

3 Claims, No Drawings

METHOD OF INHIBITING BONE RESORPTION

BACKGROUND OF THE INVENTION

1. Field of the Invention

The present invention relates to a method to inhibit the resorption of bone and more particularly, to the use of 2,2-diphosphono-azacycloalkane compounds and their water-soluble alkali metal and ammonium salts to inhibit bone resorption related to hyperparathyroidism and high turnover renal osteodystrophy.

2. The Prior Art

Bone is a dynamic tissue that regenerates throughout the life of vertebrates by turning itself over or remodeling. Healthy bone is characterized by a balance between bone loss (i.e. bone resorption) and the formation of new bone (i.e. bone mineralization). Osteoclasts are the differentiated cells responsible for the degradation of old or faulty bone. These cells are responsible for the initiation of the remodeling cycle and their activity triggers other cells, osteoblasts, to repair the excavations of the osteoclasts by laying down new healthy bone. In fact, the osteoclasts produce enzymes which break down, resorb, mineralized bone in microscopic cavities, which in healthy bone are filled by the osteoblasts creation of new bone surfaces. Active osteoblasts secrete collagen fibrils, which combine to form spiral-wound fibers of bone matrix called osteoid. Osteoblasts also cause calcium salts and phosphorus to precipitate from the blood; minerals which bond with the newly formed osteoid to mineralize the bone tissue.

In normal adult bones, the actions of osteoclastic resorption and osteoblastic formation occur at equal rates, maintaining bone mass at a constant level. The bone remodeling is triggered by a hormonal signal by parathyroid hormone (hereinafter PTH), activating the osteoclasts which attach themselves securely to bone surfaces, tunnel into the bone and begin resorption. Osteoblasts are attracted to the cavities formed, secrete collagen fibrils, which combine to form osteoid, which is mineralized to form a smooth layer of new bone.

PTH is produced by two pairs of tiny parathyroid glands located dorsal to the thyroid, though an occasional person may have more or less than four such glands. Normally, these glands are smaller than an aspirin, bean-shaped, and resemble brown fat. Enlargement of the parathyroid can occur due to disease processes related to the thyroid gland itself and cause overproduction of PTH, which is called hyperparathyroidism. When the enlargement is caused by a disease process unrelated to the thyroid, it is called secondary hyperparathyroidism. Such secondary hyperparathyroidism is a common disease in hemodialysis (i.e. renal failure) patients.

To maintain the homeostasis (i.e. balance) of calcium in the blood, PTH is released when low serum ionized calcium levels occur, directly decreasing calcium excretion. With kidney failure, calcitriol (i.e. active vitamin D) is not produced in high enough quantity to generate sufficient calcium absorption from the GI tract to maintain normal serum calcium, hypocalcemia occurs. Further, with renal failure, hyperphosphatemia occurs, contributing to the hypocalcemia. The parathyroid gland responds to this hypocalcemia by enlarging and secreting additional PTH in an effort to remedy the hypocalcemia.

Overproduction of PTH speeds up bone remodeling, causing high turnover renal osteodystrophy; wherein, high levels of PTH provoke a continuous increased rate of bone resorption. Abnormal numbers of oversized osteoclass remove calcium and phosphorus from the bone mass itself in an effort to increase the calcium level. As the effect continues, mineralization is reduced and collagen formulation while increased is disorganized and haphazard. The bones stripped of their mineral integrity, are prone to fracture and cyst formation.

It is known that biphosphonates are potential inhibitors of bone resorption that may prevent the bone loss of post menopausal women (Sato et al., J. Cell. Bio., 11:1713–1723, 1990; Sato et al., J. Clin., Invest., 88:2095–2105, 1991; Fleisch, Bone 8 (S1):S23–S28, 1990; Watts et al., N. Engl. J. Med. 323:73–79, 1990). Further, it is known that bisphosphonates can also inhibit the calcification of bioprosthetic heart valves (Levy et al., Science 228:190–192, 1985), and the formation of experimentally induced urinary stones (Fraser et al., Clin. Sci. 42:197–207,1972).

A particular family of bisphosphonates are 2,2-diphosphono-azacycloalkanes, whose general therapeutic and/or prophylatic effects related to the abnormal deposition and dissolution of difficulty soluble calcium salts in warmblooded animals are disclosed in U.S. Pat. Nos. 3,941,772 and 3,988,443. These patents disclose the use and method of such use of 2,2-diphosphono-azacycloalkanes with respect to abnormal bone deposition or dissolution in conditions such as osteoporosis and osteodystrophy. However, with respect to remodeling, only the effect of 2,2-diphosphono-azacycloalkanes on abnormal bone dissolution which cannot be replaced or are replaced only by incompletely crystallized tissue is disclosed. Such dissolution is stated as being associated with pathologically high calcium and phosphate concentrations in the blood. There is no disclosure in the patents with respect to the effect of 2,2-diphosphono-azacycloalkanes with respect to renal failure or its associated hypocalcemia. Accordingly, there is need for a means whereby in cases hyperthyroidism or secondary hyperthyroidism PTH stimulated bone remodeling can be inhibited, such as in cases of high turnover renal osteodystrophy.

SUMMARY OF THE INVENTION

The present invention is directed to a method for inhibiting the resorption of bone, concomitant with the overproduction of PTH associated with hyperparathyroidism or secondary hyperparathyroidism in humans and other warm blooded animals comprising, providing at least one pharmacologically acceptable azacycloalkane-2,2-diphosphonic compound having the formula:

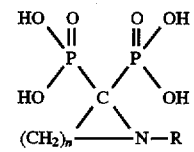

(hereinafter Formula I), wherein R is selected from the group consisting of hydrogen and alkyl having 1 to 3 carbon atoms, and n is an integer from 3 to 5; or a water-soluble salt thereof.

The ability of the method of the present invention, as detailed herein, to inhibit bone remodeling associated with pathologically low serum calcium is surprising given the prior art focus on pathologically high serum calcium and phosphate concentrations.

DETAILED DESCRIPTION OF THE PREFERRED EMBODIMENTS

As disclosed within U.S. Pat. Nos. 3,941,772 and 3,988,443, both incorporated herein by reference, diphosphonic compounds of Formula I are prepared by reacting a lactam having the formula:

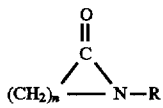

(hereinafter Formula II) in which n is an integer from 3 to 5 and R is hydrogen or alkyl having 1 to 3 carbon atoms, preferably methyl, with a phosphorous trihalide or phosphorous acid and phosphorous trihalides. The reaction product is then hydrolyzed and if required is converted into the corresponding salt.

In the preparation of Formula I compounds, Formula II lactam is reacted at about 40° C. to 150° C. with at least a stoichiometric amount of a phosphorous reactant selected from a phosphorous trihalide or a mixture of a phosphorous trihalide and phosphorous acid and thereafter subjecting the resulting reaction product to hydrolysis in an aqueous alkali media, such as an aqueous alkali metal hydroxide solution, and recovering the Formula I compound.

Suitable Formula II lactams are those having 3 to 5 carbon atoms, such as, pyrrolidone, N-methylpyrrolidone, piperidone, and caprolactam. In performing the reaction, the Formula II lactam is first melted with phosphorous acid, and $PCl_3$ is then slowly added while stirring.

The molar ratio of the lactam to the phosphorous compound ranges between 1:2 to 1:6, preferably about 1:4.

The azacycloalkane-2,2-diphosphonic acids are obtained in the form of the acids, these acids can readily be converted to the corresponding water-soluble salts, by partial or total neutralization with the corresponding bases.

The salts correspond to the following formula:

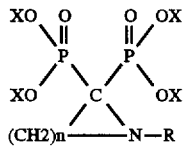

wherein, X is hydrogen, $NH_4$ or an alkali metal cation, with the proviso that at the most 3 hydrogen atoms are present and n is an integer from 3 to 5.

Specific examples of azacycloalkane-2,2-diphosphonic acids of Formula I include:
azacyclopentane-2,2-diphosphonic acid;
N-methyl-azacyclopentane-2,3-diphosphonic acid;
azaccyclohexane-2,2-diphosphonic acid; and
azacycloheptane-2,2-diphosphonic acid.

A preferred azacycloalkane-2,2-diphosphonic acid usable in the present invention is azacycloheptane-2,2-diphosphonic acid, and its sodium salt. Azacycloheptane-2,2-diphosphonic acid has a melting point of 275° C. and the formula:

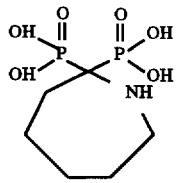

(hereinafter Formula III). Diphosphonic acids of Formula III can be prepared by first heating 1.0 moles of caprolactam and 2.0 moles of $H_3PO_3$ at 100° C. until a clear melt is obtained. After partial cooling, the clear melt is maintained at 70° C. and reacted with 2.0 moles of $PCl_3$ with stirring, for 3 hours and then allowed to stand overnight. Three liters of distilled water is added to the reaction product for the hydrolysis. The aqueous solution is boiled with activated carbon; and after filtration, the filtrate is precipitated with acetone. The white precipitate which is obtained is dissolved in water and passed over a cation exchanger. The resulting solution is concentrated, and the hydrolyzed product separated upon the addition of ethanol.

A most preferred embodiment is the disodium salt of azacycloheptane-2,2-diphosphonic acid (hereinafter disodium AHP). As detailed above, disodium AHP is derived from the crystalline azacycloheptane-2,2-diphosphonic acid by partial neutralization with its corresponding base, sodium hydroxide.

Compounds of Formula I, above, can be administered orally, subcutaneously, or intraperitoneally in the form of tablets, pills, capsules or as injectable solutions. For certain warm-blooded animals these compounds can also be used as part of the feed or feed additives.

The following examples are merely illustrative of the present invention without being deemed limitative in any manner thereof.

EXAMPLE 1

A series of bone culture experiments were carried out with a fetal rat long bone model developed to measure bone resorption, using a method described by Gaffar et al., "Effects of Potassium Peroxydiphosphate on Bone Resorption", Journal of Bone and Mineral Research, Vol. 6, Number 10, 1991. Specifically, nineteen-day-old rat fetuses were obtained from mothers which had been injected with 0.2 mCi of $^{45}Ca$ subcutaneously on day 18 of gestation. The fetuses bone shafts of the radius and ulna were dissected free of cartilage and soft tissue and precultured in BGJb medium (Life Technologies, Gaithersburg, Md.) for 18 to 24 hours. The precultured bones (28 in total) were allotted to either a control or a treatment lot; wherein, to the preculture medium of the bones in the treatment lot, disodium AHP at a level of $10^{-4}M$ was added pursuant to the present invention. This treatment lot of bones was designated Example B and the control lot of bones, to which no disodium AHP was added was designated comparative Example A.

Both these precultured lots of bones (i.e. control, comparative Example A, and treatment Example B) were then cultured in BGJb with bovine serum albumin (1 mg/ml of BSA, Sigma Chemical Company, Saint Lewis, Mo.; radioimmunoassay, RIA, grade). The cultured treatment lot was then divided in half, forming Examples B1 and B2, and the control lot also halved forming comparative Examples A1 and A2. Example B2 and comparative Example A2 were treated with a resorption stimulator, parathyroid hormone at $10^{-8}$Molar (bovine PTH-(1-84), National Institute of Health, Bethesda, Md.). Example B1 and comparative Example A1 were not treated with any resorption stimulator. The $^{45}Ca$ level of each example was measured at 2 days, the media was then changed and cultured for an additional 3 days, whereupon the $^{45}Ca$ was measured again.

The $^{45}Ca$ was counted by liquid scintillation in the medium and in trichloroacetic acid (TCA) extracts of the bone. The rate of resorption was measured as the percentage of total $^{45}Ca$ released, wherein the greater the % of $^{45}Ca$ released the greater the bone resorption. The percentages of total $^{45}Ca$ recorded at day 2 and day 5 for Examples B1 and B2 and comparative Examples A1 and A2 is recorded in Table 1, below.

TABLE 1

| Lot Preculture | Culture | 2 day % $^{45}$Ca Released (Mean +/− Std. Error) | 5 day % $^{45}$Ca Released (Mean +/− Std. Error) |
| --- | --- | --- | --- |
| A1 Control | No Resorption Stimulator | 15.3 +/− 0.9 | 23.2 +/− 2.1 |
| A2 Control | PTH | 30.1 +/− 3.1 | 76.8 +/− 8.5 |
| B1 Disodium AHP | No Resorption Stimulator | 13.2 +/− 1.5 | 18.7 +/− 1.0 |
| B2 Disodium AHP | PTH | 16.3 +/− 1.8 | 23.8 +/− 3.4 |

Analysis of variance and post hoc testing by Bonferroni's method were used to determine statistical significance (see, Hochberg et al., *Multiple Comparison Procedures*, pp. 3–5, John Wiley & Sons, N.Y.; Winer et al., *Statistical Principles in Experimental Design* 3$^{rd}$ Ed., pp. 156–166, McGraw-Hill, Inc., N.Y.). The resulting statistical analyses of the 5 day $^{45}$Ca release results show that to a p<0.05, the means presented for Examples B1 and B2 and comparative Example A1 are not significantly different, while the mean of comparative Example A2 is significantly different.

Referring to Table 1 and considering the statistical results stated above, Example B1 being statistically identical to comparative Example A1 shows that disodium AHP does not induce bone resorption. Further, Example B1 being statistically identical to Example B2 shows that disodium AHP does inhibit PTH induced bone resorption (statistically independent comparative Example A2 showing PTH's stimulation of bone resorption).

EXAMPLE 2

A pharmaceutical table composition can be formulated by wet blending 500 parts of disodium AHP and 641 parts of mannitol, with 32.5 parts of a 10% sorbitol to form wet granule, which is dried at 49° C. and screened through a 12 mesh U.S. screen (1.69 millimeter openings). 35 parts of magnesium stearate is then added as a binder and the granules are formed into a tablet by compressing the composition in a tablet compression machine.

What is claimed is:

1. A method for inhibiting bone resorption in human and other warm-blooded animals, concomitant with the overproduction of PTH associated with hyperparathyroidism or secondary hyperparathyroidism, comprising:

administering to said human and other warm blooded animals a pharmacologically acceptable, effective amount of an azacycloalkane-2,2-diphosphonic compound of the formula:

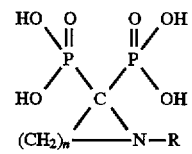

wherein, R is selected from the group consisting of hydrogen and alkyl having 1 to 3 carbon atoms, and n is an integer form 3 to 5.

2. A method according to claim 1, wherein the pharmacologically acceptable compound is a corresponding salt of the formula of claim 1, having the following formula:

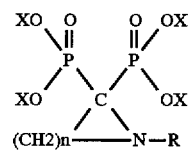

wherein, X is hydrogen, $NH_4$ or an alkali metal cation, with the proviso that at the most 3 hydrogen atoms are present and n is an integer from 3 to 5.

3. A method according to claim 1, wherein the azacycloalkane-2,2-diphosphonic compound is azacycloheptane-2,2-diphosphonic acid or its partially neutralized sodium salt.

* * * * *

UNITED STATES PATENT AND TRADEMARK OFFICE
CERTIFICATE OF CORRECTION

PATENT NO:    5,753,633

DATED:    May 19, 1998

INVENTOR(S):    Lee Allen Flippin, and Gabriel Stone Weatherhead

It is certified that error appears in the above-identified patent and that said Letters Patent is hereby corrected as shown below:

In Claim 1, column 22, lines 55 to 64, that portion of the formula reading $R^7$ should read $R^6$ and that portion should appear as follows:

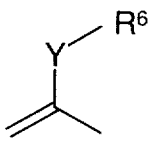

Signed and Sealed this

Eighth Day of February, 2000

Attest:

Q. TODD DICKINSON

Attesting Officer      Commissioner of Patents and Trademarks